(12) United States Patent
Burns et al.

(10) Patent No.: US 12,012,639 B2
(45) Date of Patent: Jun. 18, 2024

(54) PROCESSES FOR ISOLATION AND RECOVERY OF C5 SUGARS

(71) Applicant: University of Louisville Research Foundation, Inc., Louisville, KY (US)

(72) Inventors: Christopher T. Burns, Louisville, KY (US); Jagannadh Satyavolu, Louisville, KY (US); Michael H. Nantz, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 16/771,791

(22) PCT Filed: Dec. 11, 2018

(86) PCT No.: PCT/US2018/064974
§ 371 (c)(1),
(2) Date: Jun. 11, 2020

(87) PCT Pub. No.: WO2019/118476
PCT Pub. Date: Jun. 20, 2019

(65) Prior Publication Data
US 2021/0071273 A1    Mar. 11, 2021

Related U.S. Application Data

(60) Provisional application No. 62/597,062, filed on Dec. 11, 2017.

(51) Int. Cl.
C13K 13/00    (2006.01)
C12P 19/14    (2006.01)

(52) U.S. Cl.
CPC ............ C13K 13/002 (2013.01); C12P 19/14 (2013.01)

(58) Field of Classification Search
CPC ........ C13K 13/002; C13K 13/00; C13K 1/04; C13K 13/007; C13K 1/02; C07H 1/00;
(Continued)

(56) References Cited

U.S. PATENT DOCUMENTS 10,093,953 B2    10/2018 Gordon et al.
10,131,923 B2    11/2018 Noordam et al.
(Continued)

FOREIGN PATENT DOCUMENTS

EP        2495329 A1 *  9/2012  ........... B01D 61/422
WO  WO-2011133536 A1 * 10/2011  ............... C07H 1/08
(Continued)

OTHER PUBLICATIONS

Byju's: Is Methanol Soluble In Water [online], [retrieved on Nov. 10, 2021]. Retrieved from the Internet <URL: https://byjus.com/jee-questions/is-methanol-soluble-in-water/> (Year: 2021).*
(Continued)

*Primary Examiner* — Sheng H Davis
*Assistant Examiner* — Ritu S Shirali
(74) *Attorney, Agent, or Firm* — Jenkins, Taylor & Hunt, P.A.

(57) ABSTRACT

Processes for isolating xylose from an aqueous solution. A representative process can comprise providing an aqueous solution comprising xylose; combining a boron compound with the aqueous solution to form a boron derivative of the xylose; isolating the boron derivative of the xylose from the aqueous solution as a precipitate; dissolving the boron derivative of the xylose in a solvent; and isolating the xylose from the solvent as a precipitate using a boron capture agent.

15 Claims, 5 Drawing Sheets

(58) Field of Classification Search
CPC .... C07H 3/02; C07H 1/08; C07H 1/06; C12P 19/14
USPC ....................................................... 127/46.1
See application file for complete search history.

(56) References Cited

U.S. PATENT DOCUMENTS

| | | |
|---|---|---|
| 10,144,939 B2 | 12/2018 | Noordam et al. |
| 10,407,453 B2 | 9/2019 | Satyavolu et al. |
| 2016/0297845 A1 | 10/2016 | Satyavolu et al. |

FOREIGN PATENT DOCUMENTS

| | | | |
|---|---|---|---|
| WO | WO-2013049424 A1 * | 4/2013 | .............. B01J 27/20 |
| WO | WO 2019/118476 A1 | 6/2019 | |

OTHER PUBLICATIONS

Riera et al., Production of Furfural by Acid Hydrolysis of Corncobs, 1991, J. Chem. Tech. Biotechnol., vol. 50, pp. 149-155 (Year: 1991).*
European Search Report corresponding to EP Patent Application No. 18889861.3 dated Sep. 3, 2021.
International Search Report corresponding to International Patent Application No. PCT/US2018/064974 dated Apr. 12, 2019.
International Preliminary Report on Patentability (Chapter I of the Patent Cooperation Treaty) corresponding to International Patent Application No. PCT/US2018/064974 dated Jun. 25, 2020.
Brennan (2010) "Recovery of Sugars from Ionic Liquid Biomass Liquor by Solvent Extraction," Bioenergy Research, vol. 3, No. 2, pp. 123-133.
Duggan, P. J. et al., "Boron Acids as Protective Agents and Catalysts in Synthesis," Journal of the Chemical Society, Perkin Transactions 1, No. 11, pp. 1325-1339 (2002).
Fonseca et al. (2014) "Towards Integrated Biorefinery from Dried Distillers Grains: Selective Extraction of Pentoses Using Dilute Acid Hydrolysis," Biomass and Bioenergy, vol. 71, pp. 178-186.
Gori et al. (2015) "Isolation of C5-Sugars from the Hemicellulose-Rich Hydrolyzate of Distillers Dried Grains," ACS Sustainable Chemistry & Engineering, vol. 3, pp. 2452-2457.
Griffin et al. (2004) "Solvent extraction and purification of sugars from hemicellulose hydrolysates using boronic acid carriers," Journal of Chemical Technology and Biotechnology, vol. 79, No. 5, pp. 505-511.
Kaupp et al. (2003) "Waste-free and facile solid-state protection of diamines, anthranilic acid, diols, and polyols with phenylboronic acid," Chemistry—A European Journal, vol. 9, No. 17, pp. 4156-4160.
Rabemanolontsoa et al. (2016) "Various Pretreatments of Lignocellulosics," Bioresource Technology, vol. 199, pp. 83-91.
Reichvilser et al. (2010) "Boronic Acid Mono- and Diesters of the Aldopentoses," Carbohydrate Research, vol. 345, No. 4, pp. 498-502.
Riera et al. (1991) "Production of Furfural by Acid Hydrolysis of Corncobs," Journal of Chemical Technology and Biotechnology, vol. 50, No. 2, pp. 149-155.
Roy et al. (2007) "A Comparative Study of the Relative Stability of Representative Chiral and Achiral Boronic Esters Employing Transesterification," Monatshefte für Chemie, vol. 138, No. 9, pp. 879-887.
Roy et al. (2007) "Stability of Boronic Esters—Structural Effects on the Relative Rates of Transesterification of 2-(phenyl)-1,3,2-dioxaborolane," Journal of Organometallic Chemistry, vol. 692, No. 4, pp. 784-790.
Sun et al. (2011) "A Method for Deprotection of Alkylpinacolyl Boronate Esters," Journal of Organic Chemistry, vol. 76, No. 9, pp. 3571-3575.
Washburn et al. (1959) "Benzeneboronic Anhydride," Organic Synthesis, vol. 39, No. 3, pp. 3-6.
Office Action corresponding to Brazil Patent application Serial No. PCT/US2018/06497 dated Oct. 22, 2022.
Ricciardi et al. (2021) "Selective Extraction of Xylose From Acidic Hydrolysate-From Fundamentals To Process," ACS Sustainable Chem & Engin. vol. 9; 6632-6638.

* cited by examiner

PROCESSES FOR ISOLATION AND RECOVERY OF C5 SUGARS

CROSS REFERENCE TO RELATED APPLICATIONS

This application is a national stage filing of PCT International Application No. PCT/US2018/064974, filed Dec. 11, 2018, incorporated herein by reference in its entirety, which is based on and claims priority to U.S. Provisional Application Ser. No. 62/597,062, filed Dec. 11, 2017, the disclosure of which is incorporated herein by reference in its entirety.

TECHNICAL FIELD

The presently-disclosed subject matter relates to a process for isolating and recovering C5 sugars from an aqueous solution. In particular, the presently disclosed subject matter relates in some embodiments to a process for isolating the C5 sugar xylose from an aqueous solution and to do so in a form suitable for subsequent synthetic transformations, such as the production of a xylose-platform of biochemicals and biofuels.

BACKGROUND

Utilizing renewable resources, such as co-products from grain processing, to produce a C5-platform of biochemicals and biofuels is advantageous from the perspective of the environment, process integration, and economics, as well as energy independence and national security. Those co-products are richer in hemicelluloses and the C5 sugars derived from those co-products can be converted via chemical synthesis routes to higher-value biochemicals and high energy density components of bio-jet fuels, for example.

Hemicellulose-based sugars (e.g., xylose and arabinose) can be a platform for synthesis of a variety of industrially important chemicals that are currently derived from petroleum. Pentoses were identified by the U.S. Department of Energy in 2004 among the top candidates of valuable chemical precursors that could be produced from biomass. While numerous studies have been performed to develop processes for extraction of monosaccharides from a wide range of biomass feedstocks, these monosaccharide extraction processes have been developed as pretreatment processes to improve the downstream processes—not necessarily to isolate and use pentose sugars from the biomass feedstocks. For example, various hydrolytic techniques, such as steam explosion, steam explosion with dilute sulfuric acid, organosolv extraction, and biological treatment with white rot fungi, have all been extensively investigated as pretreatment methods to obtain hydrolyzates rich in monosaccharides.

However, the sugar concentrations in the resulting hydrolyzates are typically still lower than desired for downstream processing. As such, hydrolyzate concentration is often required before conversion to value-added chemicals or biofuels. These concentration steps may deteriorate the sugars and many of the sugar degradation compounds are toxic to the fermentation process, severely limiting yields and effectiveness of the overall processes. To address these drawbacks, one hydrolyzate treatment approach relies upon lipophilic boronic acids to form boronate complexes with cis-diol moieties of sugars, which are extracted into an organic phase by ion pairing with lipophilic quaternary ammonium cations. The resulting salts are then hydrolyzed in a clean, aqueous acidic solution to regenerate the sugars for use in subsequent fermentation or other enzymatic processes. Although this approach extracts sugars from the hydrolyzate, the utility of the extracted sugars is limited, as the aqueous sugar solution is not compatible with many biofuel or biochemical conversion schemes that require the sugars to be in dry form.

Accordingly, there remains a need in the art for a process of isolating C5 sugars, such as xylose, from aqueous solutions in a manner that allows the C5 sugars to then be converted and/or used in the production of biochemicals, polymers, and/or biofuels.

SUMMARY

Disclosed in accordance with the presently disclosed subject matter is a process for isolating xylose from an aqueous solution. In some embodiments, the process comprises: providing an aqueous solution comprising xylose; combining a boron compound with the aqueous solution to form a boron derivative of the xylose; isolating the boron derivative of the xylose from the aqueous solution as a precipitate; dissolving the boron derivative of the xylose in a solvent; and isolating the xylose from the solvent as a precipitate using a boron capture agent.

In some embodiments, the aqueous solution is provided by hydrolysis. In some embodiments, the hydrolysis comprises subjecting a biomass to dilute acid hydrolysis to form a biomass hydrolyzate; subjecting a biomass to enzymatic hydrolysis and/or digestion to form the biomass hydrolyzate; or a combination thereof. In some embodiments, the biomass is a hemi-cellulose rich agricultural biomass. In some embodiments, the hemi-cellulose rich agricultural biomass comprises a material selected from the group consisting of soy hulls from soy bean processing, rice hulls obtained from rice milling, corn fiber obtained from wet milling or dry milling, bagasse from sugarcane processing, pulp from sugar beet processing, distillers grains, switch grass, straw, hard woods, and combinations thereof.

In some embodiments, the boron compound is selected from the group consisting of a boroxine, a glycol boronic ester, a 1,2-diol boronic ester, a 1,3-diol boronic ester, a polyol boronic ester of an alkyl or aryl boronic acid, and any combination thereof. In some embodiments, the glycol boronic ester or the 1,2-diol boronic ester, or the 1,3-diol boronic ester, or the polyol boronic ester of an alkyl or aryl boronic acid is an ethylene glycol boronic ester, a propylene glycol boronic ester, a butylene glycol boronic ester, or a propanetriol boronic ester of phenyl boronic acid.

In some embodiments, the step of combining the boron compound with the biomass hydrolyzate is performed at an acidic pH or a basic pH.

In some embodiments, the boron compound can comprise a liquid boron compound or a solid boron compound, wherein when the boron compound is a solid boron compound, the method comprises adding an amount of a water-soluble alcohol to the solid boron compound to dissolve the solid boron compound.

In some embodiments, the solvent used in dissolving the boron derivative of the C5 sugar is selected from the group consisting of an aromatic solvent, a ketone solvent, an ester solvent, and combinations thereof. In some embodiments, the ester solvent is ethyl acetate. In some embodiments, the boron capture agent is 1,2propanediol. In some embodiments, the method further comprises the step of recovering an amount of the boron compound after converting and precipitating the C5 sugar from the solvent.

In some embodiments, the method further comprises the step of recovering an amount of the boroxine, or the glycol boronic ester, or the 1,2-diol boronic ester, or the 1,3-diol boronic ester, or the polyol boronic ester of an alkyl or aryl boronic acid after converting and precipitating the xylose from the solvent.

Accordingly, it is an object of the presently disclosed subject matter to provide a process for isolating xylose, such as solid, anhydrous xylose, from an aqueous solution.

An object of the presently disclosed subject matter having been stated hereinabove, and which is achieved in whole or in part by the presently disclosed subject matter, other objects will become evident as the description proceeds when taken in connection with the accompanying drawings as best described herein.

DETAILED DESCRIPTION

Figure 1:
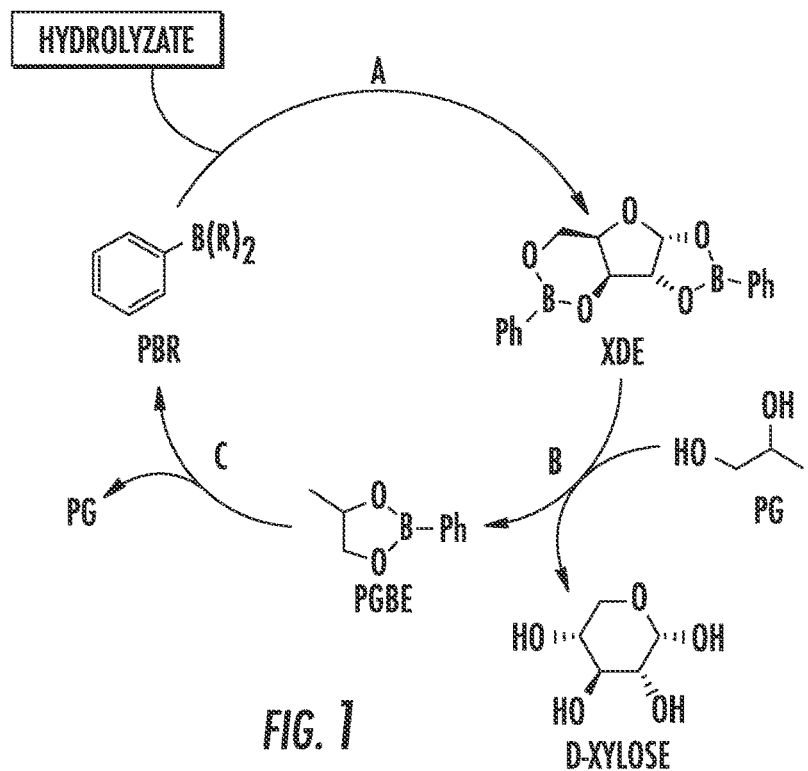
FIG. 1 is a schematic diagram showing a 3-step cycle for xylose isolation.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended), "consist of" (closed), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein the term "alkyl" refers to $C_{1-20}$ inclusive, linear (i.e., "straight-chain"), branched, saturated or at least partially and in some cases fully unsaturated (i.e., alkenyl and alkynyl) hydrocarbon chains, including for example, methyl (Me), ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

Alkyl groups can optionally be substituted (a "substituted alkyl") with one or more alkyl group substituents, which can be the same or different. The term "alkyl group substituent" includes but is not limited to alkyl (saturated or unsaturated), substituted alkyl (e.g., halo-substituted and perhalo-substituted alkyl, such as but not limited to, —$CF_3$), cycloalkyl, halo, nitro, hydroxyl, carbonyl, carboxyl, acyl, alkoxyl, aryloxyl, aralkoxyl, thioalkyl, thioaryl, thioaralkyl, amino (e.g., aminoalkyl, aminodialkyl, aminoaryl, etc.), sulfonyl, and sulfinyl.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether. Thus, examples of aryl include, but are not limited to, phenyl, naphthyl, biphenyl, and diphenylether, among others. Aryl groups include heteroaryl groups, wherein the aromatic ring or rings include a heteroatom (e.g., N, O, S, or Se). Exemplary heteroaryl groups include, but are not limited to, furanyl, pyridyl, pyrimidinyl, imidazoyl, benzimidazolyl, benzofuranyl, benzothiophenyl, quinolinyl, isoquinolinyl, and thiophenyl.

The aryl group can be optionally substituted (a "substituted aryl") with one or more aryl group substituents, which can be the same or different, wherein "aryl group substituent" includes alkyl (saturated or unsaturated), substituted alkyl (e.g., haloalkyl and perhaloalkyl, such as but not limited to —$CF_3$), cycloalkyl, aryl, substituted aryl, aralkyl, halo, nitro, hydroxyl, acyl, carboxyl, alkoxyl, aryloxyl, aralkyloxyl, thioalkyl, thioaryl, thioaralkyl, amino (e.g., aminoalkyl, aminodialkyl, aminoaryl, etc.), sulfonyl, and sulfinyl.

In some embodiments, the presently disclosed subject matter provides a process for isolating xylose from an aqueous solution. In some embodiments, the process comprises providing an aqueous solution comprising xylose; combining a boron compound with the aqueous solution to form a boron derivative of the xylose; isolating the boron derivative of the xylose from the aqueous solution as a precipitate; dissolving the boron derivative of the xylose in a solvent; and isolating the xylose from the solvent as a precipitate using a boron capture agent. The presently-disclosed subject matter is based, at least in part, on the development and demonstration of an improved process for extraction and isolation of C5 sugars, and xylose in particular, from an aqueous solution. In some embodiments, the presently disclosed subject matter provides for the selective isolation of xylose from an aqueous solution comprising other C5 sugars. As compared to other sugars (i.e., glucose, arabinose) the rapid reactivity of xylose with the disclosed boron reagents coupled with the poor water solubility of the xylose boron diester leads (e.g., XDE) to the observed selectivity for xylose. In some embodiments, the xylose is converted to a xylose-platform for the production of biochemicals and biofuels, such as bicyclopentane (BCP).

The aqueous solution can be provided from any suitable source. By way of example and not limitation, in some embodiments a fermentation broth, and, at least in part, for economic reasons, a hemicellulose rich "captive" agricultural biomass is used to selectively extract C5 sugars and xylose in particular. As such, in some embodiments, a process for isolating a C5 sugar, and xylose in particular, is provided that includes an initial step of providing a biomass hydrolyzate including a C5 sugar, and xylose in particular, such as what is present in a hemicellulose-rich biomass. In some embodiments, the aqueous solution is provided by hydrolysis. In some embodiments, the hydrolysis comprises a dilute acid hydrolysis, an enzymatic hydrolysis and/or digestion; or a combination thereof.

As would be understood by those skilled in the art, the terms "cellulose" and "hemicellulose" are used herein to refer to organic compounds present in almost all plant cell walls. "Cellulose" is generally used to refer to an organic compound with the formula $(C_6H_{10}O_6)n$ that forms a polysaccharide consisting of a linear chain of several hundred to many thousands of β(1→4) linked D-glucose units. In contrast to cellulose, the term "hemicellulose" is used herein to refer to any of several heteropolymers or matrix polysaccharides that are present along with cellulose in almost all plant cell walls. Indeed, by weight, the largest component of plant matter is lignocellulosic material; a mixture of cellulose, hemicellulose, and lignin. When these materials are subjected to either acid or enzymatic hydrolysis to divide the molecules into their constituent sugars, the hemicellulose breaks down to form five-carbon or C5 sugars, such as xylose, whereas the cellulose chain splits into glucose (a six-carbon sugar or "C6 sugar").

In this regard, the terms "C6 sugar" or "hexose" are used interchangeably herein to refer to monosaccharides that include six carbon atoms, that typically have the chemical formula $C_6H_{12}O_6$, and that are classified according to their functional groups, with aldohexoses having an aldehyde at position 1 of the C6 sugar, and ketohexoses having a ketone at position 2 of the C6 sugar. The terms "C5 sugar" or "pentose," on the other hand, are used interchangeably herein to refer to monosaccharides that include five carbon atoms, and that can be generally organized into two groups, namely aldopentoses, which have an aldehyde functional group at position 1 of the C5 sugar, and ketopentoses, which have a ketone functional group in position 2 or 3 of the C5 sugar.

To produce a C5-rich biomass hydrolyzate or, in other words, a C5-rich biomass subjected to hydrolysis, hemicellulose-rich materials are typically first provided. Suitable hemicellulose-rich materials and/or hemicellulose-rich agricultural biomasses include any material and/or agricultural biomass having a hemicellulose concentration of at least 10%, at least 15%, at least 20%, at least 25%, at least 30%, between 10% and 99%, between 10% and 90%, between 15% and 75%, between 15% and 50%, or any combination, sub-combination, range, or sub-range thereof. Exemplary hemicellulose-rich agricultural biomasses that can be used in this regard include, but are not limited to: soy hulls from soybean processing, rice hulls from rice milling, corn fiber from wet milling or dry milling, bagasse from sugarcane processing, pulp from sugar beets processing, distillers grains, switch grass, straw, hard woods, and the like, and combinations thereof.

Upon providing the hemicellulose rich biomass, in some embodiments, to ensure an effective amount of C5 sugars are isolated from the biomass in subsequent hydrolysis steps, the biomass is first subjected to a pretreatment procedure. The pretreatment procedure, performed prior to hydrolysis, provides a pretreated biomass having an enriched fiber fraction (i.e., enhances the fiber value of the biomass). For example, in some embodiments, the pretreatment procedure includes a screening procedure that makes use of a sieve (e.g., a sieve with 0.85 mm openings) to produce a coarse fraction that does not pass through the openings thereof. The coarse fraction forms the pretreated biomass, which typically has a higher fiber content as compared to the untreated hemicellulose rich biomass. As will be understood by those skilled in the art, the sieve is not limited to 0.85 mm openings and may include any other suitable sized openings based upon the biomass material and/or the amount of biomass to be retained as the coarse fraction.

In some embodiments, the pretreatment procedure also includes subjecting the coarse fraction and/or biomass to sonication, which increases breakdown of the coarse fraction and provides a material on which hydrolysis can more effectively and efficiently be performed. For example, following the screening procedure, sonication may include adding the coarse fraction to a liquid, such as water, and then sonicating the liquid/coarse fraction mixture with any suitable sonication device. Suitable sonication devices include any device capable of applying sound energy to the biomass and/or coarse fraction, such as, but not limited to, an ultrasonic homogenizer. After sonication and prior to hydrolysis, the coarse fraction and/or biomass is dewatered through any method for separating the coarse fraction from the water, such as, but not limited to, passing the liquid/coarse fraction through a mesh screen.

To produce a C5-rich hydrolyzate, in some embodiments, a mild dilute acid hydrolysis is performed on the hemicellulose rich biomass and/or the pretreated biomass. The mild dilute acid hydrolysis provides selective hydrolysis of the biomass and a cleaner C5-rich hydrolyzate with minimal degradation products. Any suitable device may be used for the dilute acid hydrolysis, including, but not limited to, a percolation reactor. For example, mild dilute acid hydrolysis of the biomass may be performed in a large volume percolation reactor with liquid recirculation, which permits an acid solution to be passed through a fibrous biomass material, then heated and recirculated through the reactor.

In this regard, in some embodiments of the presently disclosed subject matter, to produce a sufficient hydrolyzate, an amount of solid biomass material is initially placed in a reactor and is then exposed to an acid solution that is percolated through the material at an elevated temperature and for a sufficient amount of time to allow the hydrolysis reaction occur. In some embodiments, the elevated temperatures used in accordance with the hydrolysis procedure range from about 100° C. to about 150° C. (e.g., about 100° C., 105° C., 110° C., 115° C., 120° C., 125° C., 130° C. 135° C., 140° C., 145° C., or 150° C.) with a reaction time of about 30 to about 120 minutes (e.g., about 30, 35, 40, 45, 50, 55, 60, 65, 70, 75, 80, 85, 90, 95, 100, 105, 110, 115 or 120 minutes). Of course, a number of acids can be used to effectuate a sufficient hydrolysis reaction including, in some embodiments, mineral acids such as sulfuric acid and hydrochloric acid (HCl), etc.; nitric acid ($HNO_3$); para-toluenesulfonic acid; formic acid; acetic acid; methane sulfonic acid; and trifluoroacetic acid; and dicarboxylic acids, such as oxalic acid, maleic acid, etc. In some embodiments, the acid can be provided at a concentration of about 0.2 wt % to about 5.0 wt %, including about 0.2, 0.5, 0.7, 1.0, 1.2, 1.5, 1.7, 2.0, 2.2, 2.5, 2.7, 3.0, 3.2, 3.5, 3.7, 4.0, 4.2, 4.5, 4.7, or 5.0 wt %. For further explanation and guidance relating to reaction conditions for producing a biomass hydrolyzate, see, e.g., Fonseca, et al., Biomass and Bioenergy, 21 (2014), 178-186 as well as Riera, et al. Journal of Chemical Technology and Biotechnology, 1991, 50 (2), 149-155, both of which are incorporated herein by reference in their entirety. Representative processes are also disclosed in Published U.S. Patent Application No. 2016-0297845 and U.S. Pat. No. 10,093,953, herein incorporated by reference in their entireties.

In some embodiments, the hydrolysis comprises an enzymatic hydrolysis and/or digestion. The enzymatic hydrolysis and/or digestion can be carried out in accordance with standard techniques recognized in the art, such as but not limited to those described in Rabemanolontsoa and Saka, Bioresource Technology 199 (2016) 83-91, which is incorporated herein by reference in its entirety. Representative processes are also disclosed in U.S. Pat. Nos. 10,144,939 and 10,131,923, herein incorporated by reference in their entireties. Samples prepared by enzymatic hydrolysis and/or digestion can be purchased commercially as well. As a further example, hemicellulase (a mixture of xylanase, mannanase, and other C5 hydrolyzing enzymes) can be used to breakdown hemicellulose polymers in a lignocellulosic biomass to monomeric sugars in an aqueous solution. The hydrolysis is typically done under ambient conditions depending on the thermal stability of the hemicellulase enzyme.

Following the hydrolysis, the hydrolyzate is then, in certain embodiments, utilized in a process of isolating a C5 sugar as described herein. In some embodiments, the process comprises providing an aqueous solution comprising xylose; combining a boron compound with the aqueous solution to form a boron derivative of the xylose; isolating the boron derivative of the xylose from the aqueous solution as a precipitate; dissolving the boron derivative of the xylose in a solvent; and isolating the xylose from the solvent as a precipitate using a boron capture agent.

The boron compound can be any suitable boron-containing compound as would be apparent to one of ordinary skill in the art upon a review of the instant disclosure. In some embodiments, the boron compound is a boronic acid, such as but not limited to phenyl boronic acid (PBA), naphthalene-2-boronic acid, 4-biphenylboronic acid, pyridine-4-boronic acid (cas #1692-15-5), pyridine-3-boronic acid (cas #1692-25-7) para-tolueneboronic acid (cas 5720-05-8). 3,5-dimethylphenylboronic acid (cas #17975-69-8), 4-nitrophenylboronic acid (cas #24067-17-2), 4-(Dimethylamino) phenylboronic acid (cas #28611-39-4). In some embodiments, the boron compound is a boroxine, such as but not limited to triphenylboroxine (TPB), and a boroxine derived from any of the above-mentioned boronic acids. In some embodiments, the boron compound comprises a substituted or unsubstituted polyol boronic ester of an alkyl or aryl boronic acid. In some embodiments, the boron compound comprises a glycol boronic ester, a 1,2-diol boronic ester, a 1,3-diol boronic ester, a 1-2 amino diol boronic ester, a 1-3 amino diol boronic ester, or a triol boronic ester of an alkyl or aryl boronic acid. In some embodiments two or more different boron compounds are combined with the aqueous solution. Additional boron compounds, such as those that work well with xylose, including to selectively isolate xylose, include but are not limited to 4,5-dimethyl-2-phenyl-1,3,2-dioxaborolane (cas #6638-68-2); phenylboronic acid 1,2-propanediol ester (cas #4406-75-1); 2-phenyl-1,3,2-dioxaborolane (cas #4406-72-8); 2-phenyl-1,3,2-dioxaborinane (cas #4406-77-3); mixture of glycerol 1,2-phenylboronate and glycerol 1,3-phenylboronate; dimethyl phenyl boronate (CAS #: 13471-35-7); diethyl phenyl boronate (Cas #31044-59-4); phenylboronic acid neopentylglycol ester (cas #5123-13-7). Also, representative structural formulae for a boron compound that is used for the isolation of xylose include aryl-B(OR)$_2$, and alkyl —B(OR)$_2$, wherein aryl and alkyl can be substituted or unsubstituted alkyl or aryl as defined hereinabove, such as, but not limited to, a group as present on one of the above-presented examples and wherein R can be the same or different, and can be any suitable moiety. In some embodiments, each R is selected from H, alkyl, substituted alkyl, aryl, and substituted aryl. In some embodiments, two R groups together can form an alkylene group (i.e., a bivalent aliphatic hydrocarbon group that can be substituted or unsubstituted with one or more alkyl group substituents, such as, but not limited to a substituted or unsubstituted C2 or C3 alkylene group) or a group having the formula —B(R')—O—B(R')—, wherein each R' is selected from the group consisting of H, alkyl, substituted alkyl, aryl, and substituted aryl. In some embodiments, each R can be a group such as, but not limited to, a R group as present on one of the above-listed examples. See also FIG. 3 for a representative boron compound reacting with xylose.

In some embodiments, the boron compound can comprise a liquid boron compound or a solid boron compound. In some embodiments, when the boron compound is a solid boron compound, the process comprises adding an amount of a water-soluble alcohol to the solid boron compound to dissolve the solid boron compound. Representative water-soluble alcohols include but are not limited to methanol, ethanol, propanol, and/or isopropanol. Due to water insolubility of solid boron reagents, the alcohol makes a solution with no solid present. This then mixes rapidly with the aqueous xylose solution, allowing the formation of the xylose boron diester to occur rapidly. For liquid boron reagents, which are also insoluble in water, no alcohol is employed since the liquid/liquid interface allows for rapid reaction when the reaction is stirred rapidly.

In some embodiments, the combining of the boron compound with the aqueous solution occurs at a neutral pH, e.g. about pH 7. But, it is not required that the pH be adjusted to neutral. In some embodiments, the combining of the boron compound with the aqueous solution occurs at a basic pH. The combining can occur at any basic pH, including by way of example and not limitation, about pH 8 and about pH 9, or any pH ranging from about pH 7.1 to about 9. Further, in accordance with a surprising aspect of the presently disclosed subject matter, the combining of the boron compound with the aqueous solution occurs at acidic pH. The combining can occur at any acidic pH, including by way of example and not limitation, about pH 2, about pH 3, about pH 4, about pH 5, and about pH 6, or any pH ranging from about pH 2.0 to about 6.0. This is in marked contrast to prior processes which require the pH of the aqueous solution to be adjusted to close to neutral pH before the addition of a boron compound.

The combining of the boron compound with the aqueous solution yields a boron derivative of the C5 sugar, e.g. xylose. By way of further example and not limitation, the combining of the boron compound with the aqueous solution yields a boron derivative comprising a furanose monoester or diester of the C5 sugar (e.g., xylose diester (XDE)). In this regard, in some embodiments, the glycol or 1-2 or 1-3 diol or triol included in the glycol boronic ester or the 1-2 or 1-3 diol or triol boronic ester of an alkyl or aryl boronic acid can comprise a number of different glycols, diols, or triols including, but not limited to, norbornaanediol (ND), 2,3-butanediol, ethylene glycol, and propylene glycol. Similarly, the alkyl or aryl boronic acid can also comprise of a number of different alkyl or aryl boronic acids, such as phenyl boronic acid (PBA), naphthalene-2-boronic acid, and 4-biphenylboronic acid. In some embodiments of the presently disclosed subject matter, the glycol is propylene glycol and the alkyl or aryl boronic acid is PBA, such that the glycol boronic ester of an alkyl or aryl boronic acid is a propylene glycol boronic ester of phenyl boronic acid (PGBE). Additional boron compounds, such as those that work well with xylose, including to selectively isolate xylose, include but are not limited to 4,5-dimethyl-2-phenyl-1,3,2-dioxaborolane (cas #6638-68-2); phenylboronic acid 1,2-propanediol ester (cas #4406-75-1); 2-phenyl-1,3,2-dioxaborolane (cas #4406-72-8); 2-phenyl-1,3,2-dioxaborinane (cas #4406-77-3); mixture of glycerol 1,2-phenylboronate and glycerol 1,3-phenylboronate; dimethyl phenyl boronate (CAS #: 13471-35-7); diethyl phenyl boronate (cas #31044-59-4); phenylboronic acid neopentylglycol ester (cas #5123-13-7). Also, Representative structural formulae for a boron compound that is used for the isolation of xylose include aryl-B(OR)$_2$, and alkyl —B(OR)$_2$, wherein aryl and alkyl can be substituted or unsubstituted alkyl or aryl as defined hereinabove, such as, but not limited to, a group as present on one of the above-presented examples and wherein R can be the same or different, and can be any suitable moiety. In some embodiments, each R is selected from H, alkyl, substituted alkyl, aryl, and substituted aryl. In some embodiments, two R groups together can form an alkylene group (i.e., a bivalent aliphatic hydrocarbon group that can be substituted or unsubstituted with one or more alkyl group substituents, such as, but not limited to a substituted or unsubstituted C2 or C3 alkylene group) or a group having the formula —B(R')—O—B(R')—, wherein each R' is selected from the group consisting of H, alkyl, substituted alkyl, aryl, and substituted aryl. In some embodiments, each R can be a group such as, but not limited to, a R group as present on one of the above-listed examples.

In accordance with the presently disclosed subject matter, any suitable amount of boron compound can be added to provide complexation with the C5 sugar (xylose in particular). Suitable amounts of boron compound include, but are not limited to, boron compound:xylose molar ratios of between 1 and 12, between 2 and 12, between 3 and 11, between 4 and 12, between 2 and 10, between 6 and 10, between 4 and 8, between 5 and 7, between 7 and 9, about 6, about 8, or any combination, sub-combination, range, or sub-range thereof. In some embodiments, about 2 equivalents of boron compound (e.g., PGBE) are utilized per equivalent of C5 sugar (e.g., xylose) included in the aqueous solution. In some embodiments of the presently disclosed subject matter, and without wishing to be bound by any particular theory or mechanism, it is believed that the use of PGBE is selective for the isolation of xylose, as esters of other sugars that might be present in the aqueous solution do not precipitate. Of course, it is further provided, however, that differently alkyl or aryl boronic esters may be used for the isolation of xylose.

The boron derivative of the C5 sugar (e.g., xylose), which can be a furanose ester or diester of the C5 sugar (e.g., xylose), that is produced after combining the boron compound with the aqueous solution, is dissolved through the addition of an amount of solvent. In some embodiments, the solvent is an aromatic solvent, such as toluene, benzene, or xylene; a ketone solvent, such as acetone, 3-pentanone, or 2-butanone; or an ester solvent, such as ethyl acetate or gamma-valerolactone. Combinations of such solvents can be employed. In some embodiments, then, the presently disclosed process makes use of ethyl acetate 3-pentanone or 2-butanone as a solvent; toluene, benzene, or xylene as a solvent; or acetone or gamma-valerolactone as a solvent. In some embodiments, the solvent can be considered a "green" solvent that is generally regarded as environmentally-friendly.

Once a solution comprising the solvent and the boron derivative of the C5 sugar is formed, a boron capture agent is added to the solution. This causes the C5 sugar (e.g., xylose) to precipitate from the solvent wherein it can be isolated. By way of elaboration and not limitation, an amount of a glycol or a 1-2 or 1-3 diol or triol is added to the solution to thereby drive the cleavage of the C5 sugar diesters as it has been observed that the formation of a thermodynamically more stable boronic ester can drive the cleavage of boronic esters of six- and even certain five-membered ring 1,2-diols, such as are present in the C5 sugar diesters (e.g., XDE) of the presently-disclosed subject matter. Thus, the glycol or a 1-2 or 1-3 diol or triol are representative boron capture agents. A particular boron capture agent is 1,2 propane diol. In some embodiments, by making use of such "boron capture agents," the C5 sugars (e.g., xylose) are then precipitated and recovered in pyranose form that, in turn, is readily isolated via filtration. In some embodiments, the xylose is solid, anhydrous xylose. The solid C5 sugars (e.g., xylose) may then be used for conversion of the sugars to biochemicals or biofuels, while the boron reagents, such as but not limited to the glycol boronic ester or the 1-2 or 1-3 diol or triol boronic ester of an alkyl or aryl boronic acid (e.g., PGBE) can be recovered for use in subsequent reactions. Additional examples of boron capture agents include but are not limited to 1,3-propanediol, 2,3-propanediol, ethylene glycol, and glycerol.

By making use of the above-described process in accordance with the presently disclosed subject matter, the process offers several benefits that improve current process economics, improve boron compound recovery, and reduce xylose production cost. In particular, in some embodiments of presently described process, the boron compound is added directly to the aqueous without a need for a solvent to dissolve the boron reagent. That is, the boron compound can be added in liquid form. In addition, prior processes required the pH of the aqueous solution to be adjusted to close to neutral pH before the addition of a boron reagent and also required the liquor remaining after C5 sugar diester separation to be sent to waste water treatment. In some embodiments, the process described herein, however, eliminates the need for pH adjustment and the acidic liquor remaining after XDE removal can be recycled into a further hydrolysis process step. In this regard, the potential for acid recovery and recycle further allows the use of less corrosive dicarboxylic acids (DCA) during hydrolysis of the biomass, which, in turn, offers better selectivity to hemicelluloses, minimizes formation of hem icellulose degradation products, and lowers the capital cost for hydrolysis reactors.

The presently-disclosed subject matter thus provides in some embodiments to a process for isolating and recovering xylose from an aqueous solution. In particular, the presently-disclosed subject matter relates to a process for isolating xylose from a biomass hydrolyzate that makes use of a minimal number of process steps and ambient process conditions to separate and isolate C5 sugars from a hydrolyzate stream and to do so in a form suitable for subsequent synthetic transformations, such as the production of a C5-platform of biochemicals and biofuels.

The presently-disclosed subject matter is further illustrated by the following specific but non-limiting examples.

EXAMPLES

In the following Examples 1 and 2, a xylose isolation and precipitation process is described in which the solvents used were (a) $H_2O$ for formation of a hydrolyzate, and (b) a minimum amount of alcohol (preferably ethanol) to solubilize a boron reagent, triphenyl boroxine (TPB), and allow it to mix with the aqueous hydrolyzate. The following Examples 1 and 2, however, further describe an improved and novel xylose isolation and precipitation process in which a different boron reagent, namely the propylene glycol boronic ester of phenyl boronic acid (PGBE), was used instead of TPB in the formation of xylose diester (XDE) and in which no solvent is utilized as neat PGBE was mixed directly with the aqueous hydrolyzate to form XDE, which then precipitates from the solution. Moreover, in that novel process, XDE was not extracted from the hydrolyzate using toluene as toluene was completely removed from the XDE formation and isolation process. The XDE precipitated from the hydrolyzate/boron reagent solution and was collected by filtration. The collected XDE was then simply washed with $H_2O$.

Example 1—Three-Step Cycle for Xylose Production (FIG. 1)

Process Step A. In the initial step of the process, the production of xylose diester (XDE) using a phenyl boron reagent (PBR) (Step A) involved the reaction of the PBR and xylose to form xylose diester XDE (PhB)2(D-XylfH-4). XDE cleanly precipitated from the mixture and could be isolated by simple filtration. When arabinose or glucose were present at low concentrations in the hydrolyzate (pH=7.5), only XDE precipitated and the boronic diesters of arabinose and glucose remained in solution allowing for a simple separation method. In this regard, the presently-described xylose isolation process was developed using hydrolyzate containing D-xylose as the principal C5 sugar (ca. 16-24 mg/mL D-xylose by HPLC) among several other components.

Process Step 8. In the second step of the process, a trans-esterification using 1,2-propanediol (PG) and xylose precipitation (Step 8) exploited an observation that formation of a thermodynamically more stable boronic ester could drive the cleavage of boronic esters of six and even certain five-membered ring 1,2-diols, such as are present in XDE. In particular, in the second step, excess propylene glycol (PG, FIG. 1) was reacted with a solution of XDE. In this process, xylose precipitated as D-xylopyranose and the solution contained the corresponding phenylboronic ester of PG (PGBE). After the xylose was removed from the PGBE/PG solution by filtration, the crystalline xylose was allowed to dry. $^1$H NMR spectral characterization of the precipitated xylose indicated a high level of purity (>99%, ca. 98:2 mixture of α:β anomers) as no contamination from other sugars or organic byproducts from the DDG hydrolyzate were noted. The unreacted PG could then be recovered and used again as it readily separated from the non-polar PGBE after removal of solvent from the filtrate.

Process Step C. In the third step of the process, the recovery of PBR (Step C) was required to lower operational costs through reuse of the PBR for subsequent runs of the xylose isolation cycle. One route that was explored was the vigorous mixing of PGBE with water to effect hydrolysis of the boronic ester moiety and precipitation of a PBA/triphenylboroxine (TPB, see below and FIG. 2) mixture. The white solid was isolated via filtration in 79% yield and recycled. PG can be recovered from step C.

Example 2—Two Step Cycle for Xylose Production

Figure 2:
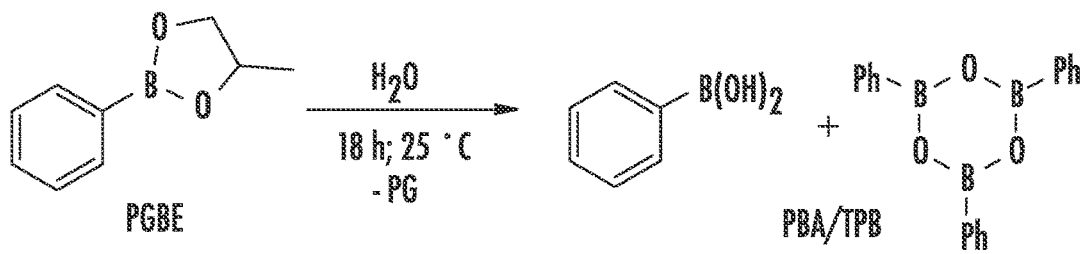
FIG. 2 is a schematic diagram showing a reaction of a propylene glycol boronic ester of phenyl boronic acid (PGBE) with $H_2O$ to form phenyl boronic acid (PBA) and triphenylboroxine (TPB).

In the above-described methods, 8 equivalents of a PBR (stated as phenyl boronic acid by the manufacturer) per xylose produced a toluene extract that contained XDE, unreacted PBR, and the boronic diester of arabinose (ADE). As described below, however, the process has now been improved to reduce the PBR equivalents used in the XDE precipitation reaction from 8 to 2. That development significantly reduced the amount of unreacted PBR that was in the hydrolyzate after XDE harvesting. The second issue was the molecularity of the phenyl boron reagent used in the process. PBA readily underwent a dehydration reaction in dry air at 25° C. to form triphenylboroxine (TPB). In fact, an analysis of purchased PBA (98% pure by HPLC analysis) by $^1$H NMR spectroscopy in $CDCl_3$ showed that varying amounts of TPB were always present. In one case, a brand new 1 Kg bottle of PBA was analyzed shortly after the bottle was opened and the composition of the white solid was determined to have a ratio of TPB to PBA of 95:5. In this regard, while some success was found in using 2 equivalents of TPB in the XDE precipitation reaction, an additional approach to further improve boron reagent recovery was developed in which PGBE was used in place of PBA (or TPB) to form XDE from hydrolyzates. As mentioned above, hydrolysis of PGBE in water yielded PBA/TPB in moderate yields (FIG. 2). Although the PBA/TPB mixture was isolated by simple filtration (PG was very soluble in $H_2O$) the lower yield of PBA/TPB was due to the unexpected high solubility of PBA in water, 2.5 g PBA per 100 g $H_2O$ at 25° C. Attempts to isolate more PBA/TPB by concentration of the aqueous solution were not straightforward due to the sublimation of PBA while water was being removed under vacuum. One possibility was to switch to a different solvent with a lower boiling point such as ethanol but PBA/TPB and PG are highly soluble in ethanol (a 1 g mixture of PBA/TPB dissolves in roughly 3 mL ethanol). As such, and as described below, another option had to be developed.

Figure 3:
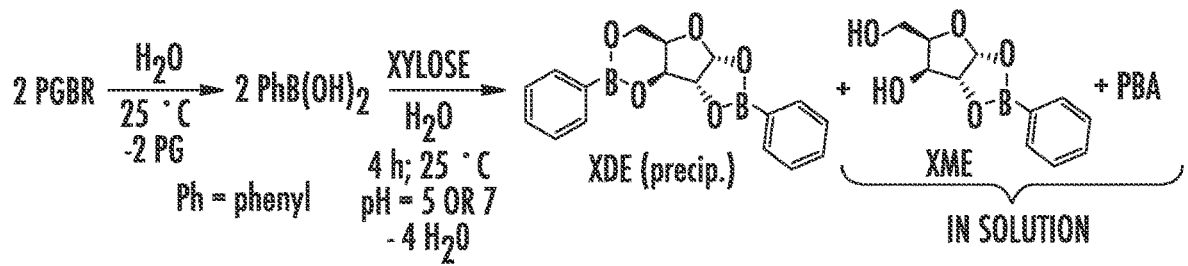
FIG. 3 is a schematic diagram showing the formation of a xylose monoester (XME) and the precipitation of xylose diester (XDE) from xylose and PGBE.

Replacement of PBA/TPB with PGBE to form XDE. Whereas PGBE was a non-polar liquid, when suspended in water and mixed vigorously with hydrolyzate, PGBE formed PBA in-situ which reacted with xylose to produce a white precipitate (XDE, FIG. 3). It was thus discovered that PGBE can be used to form XDE and allow for the realization of a 'closed-loop' in the presently-described xylose isolation process. When the PGBE hydrolysis reaction was conducted using 1 L of a xylose rich hydrolyzate (41.1 g/L, 2 equivalents of PGBE per xylose; 2.7 g/L of arabinose present) at pH of 5, XDE was formed in 61% yield and could be collected by filtration (FIG. 3). A small amount of TPB (<1%) was observed with the precipitated XDE. XDE was extremely insoluble in $H_2O$ so the moderate yields of precipitated XDE obtained were surprising. Without wishing to be bound by any particular theory or mechanism, the formation of XDE likely proceeded through the formation of the xylose furanose monoester (XME) which was soluble in $H_2O$ (FIG. 3). In further experiments, attempts to independently synthesize XME were unsuccessful. It was believed that XME reacted with a second equivalent of in-situ generated PBA (from PGBE hydrolysis) to form XDE which be immediately precipitated from the hydrolyzate. When XDE depleted solutions were concentrated, additional white precipitate appeared and was isolated by filtration. The solid was identified by $^1$H NMR as XDE with a trace amount of TPB present (<0.5%). The total yield (initial and second batch of white solid collected after concentration/filtration) of isolated XDE was 81.51 g (92%) based on the amount of xylose present in the hydrolyzate as determined by HPLC analysis (theor. yield=88.13 g XDE). When the small amount of recovered TPB was included <13% of the PGBE used in this reaction and 10% of the initial xylose were unaccounted for in the overall material balance. Use of PGBE in the formation of XDE from hydrolyzates allowed the use of a boron reagent with consistent molecularity as compared to PBA/TPB. When dilute aqueous acidic solutions of xylose were heated to concentrate the xylose, xylose decomposition to furfural and acetic acid was observed. The formation of XME/XDE precipitation prevented the xylose from participating in undesired side reactions. This was believed to be an important discovery that allowed the xylose isolation process to be carried out with little xylose decomposition while recovering the maximum amount of phenyl boron reagent (e.g., PGBE) used in the process, and thus reducing operating costs.

Figure 4:
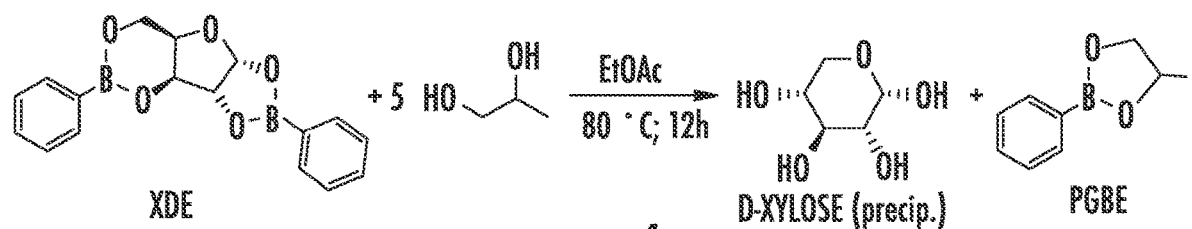
FIG. 4 is a schematic diagram showing the conversion of XDE into xylose and PGBE.

Conversion of XDE to Xylose in EtOAc. In Example 1, toluene was used as the solvent for the conversion of XDE to xylose in 92% isolated yield. This was not ideal both from an isolation and an environmental standpoint. Propylene glycol (PG, 5 equiv.) had limited solubility in toluene so while the starting XDE was very soluble in toluene when the xylose precipitated from toluene, it mixed with the undissolved PG and created a viscous, gelatinous residue. After the toluene/PGBE solution was decanted away, diethyl ether or ethanol was then required to solubilize the excess PG to allow for the isolation of crystalline xylose by filtration. In the presently described process, that method was modified to now use EtOAc as the reaction solvent (FIG. 4). Both XDE and PG were soluble in EtOAc at 25° C. and xylose precipitated from the reaction mixture as a crystalline solid that was isolated in 82% yield via filtration, leaving the excess PG, PGBE and unreacted XDE dissolved in EtOAc. When the reaction was performed at 80° C. the yield of xylose increased to 89%, which was similar to the yield obtained using toluene/$Et_2O$ at 25° C. After removal of EtOAc from the filtrate, unreacted PG and PGBE/XDE formed two distinct layers due to their very different polarities and were easily separated.

The PGBE and unreacted XDE were separated using 2-propanol, and pure PGBE was isolated by the removal of the 2-proponal. Both the EtOAc and 2-proponal could be recovered and reused in this reaction. This new green process allowed for the isolation of pure xylose by filtration, recovery of PGBE and PG for use in subsequent reactions, and isolation of unreacted XDE so that phenyl boron reagent recovery was maximized. The use of EtOAc made the process more cost effective, safer, and much more environmentally friendly.

The PGBE/XDE mixture (that contains a small amount of unreacted XDE) discussed in the previous paragraph can be separated using 2-proponal, as the solvent, to give pure PGBE and a small amount of XDE. The pure PGBE can then be recycled and used in step one of this xylose isolation process. The small amount of XDE can be (either pooled with other batches of XDE or used as is) reacted with PG to provide more pure solid xylose and PGBE. This purification step shows that the process can be optimized to provide maximum recovery of xylose as well as all the chemicals that are used and recycled in this process with little effort.

Figure 5:
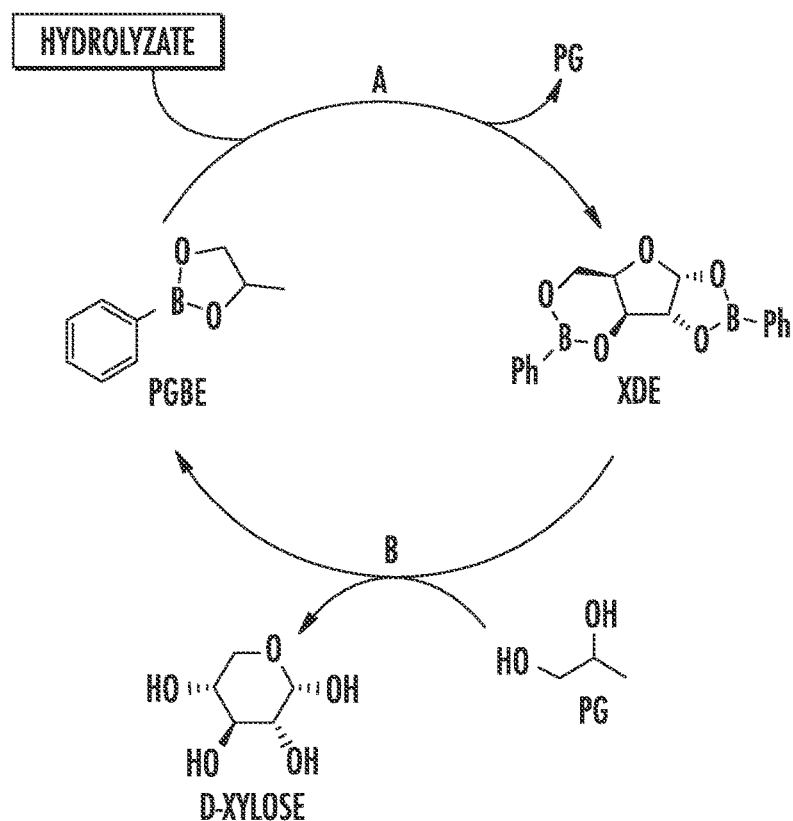
FIG. 5 is a schematic diagram showing a two-step cycle for xylose isolation in accordance with the presently disclosed subject matter.

Removal of PBR Recovery Step. As disclosed in the above sections, it was no longer necessary to convert the isolated PGBE to PBA/TPB in $H_2O$. Instead, the PGBE isolated in the formation of xylose from XDE (which is >95%) was used in the formation of XDE from the hydrolyzates (FIG. 5). The removal of the PGBE to PBA/TPB step in the process eliminated the potential for loss of boron due to the high solubility of PBA in $H_2O$ and made the isolation of xylose from hydrolyzates a two-step process. The use of neat PGBE in the front end of the process made the overall procedure a closed loop with regards to the phenyl boron reagent and greatly increased the costs effectiveness of the technology.

pH Effects: Corn fiber from dried distiller grains (DDG) provided acidic hydrolyzates (pH=2) with a low concentration of xylose (16.7 g/L). The xylose concentration could be increased by neutralization of the hydrolyzate to pH=5 followed by concentration under vacuum at 45° C. This operation resulted in hydrolyzates that contained increased xylose concentrations (24-27 g/L) and could be used in our process at pH=5 with no further neutralization required with up to 80% of available xylose, as XDE, isolated. A less labor-intensive process was to use corn fiber from wet milling in place of corn fiber from DDG. Corn fiber from wet milling provided acidic hydrolyzates (pH=2 and 5) with a much higher concentration of xylose (27 g/L). Fermentation solutions (41 g/L xylose) were further obtained for optimization and scalability studies of the xylose isolation protocol. The fermentation solutions were used as received (pH=5.2) and up to 80% of available xylose, as XDE, was isolated during our preliminary test reactions.

Figure 6A:
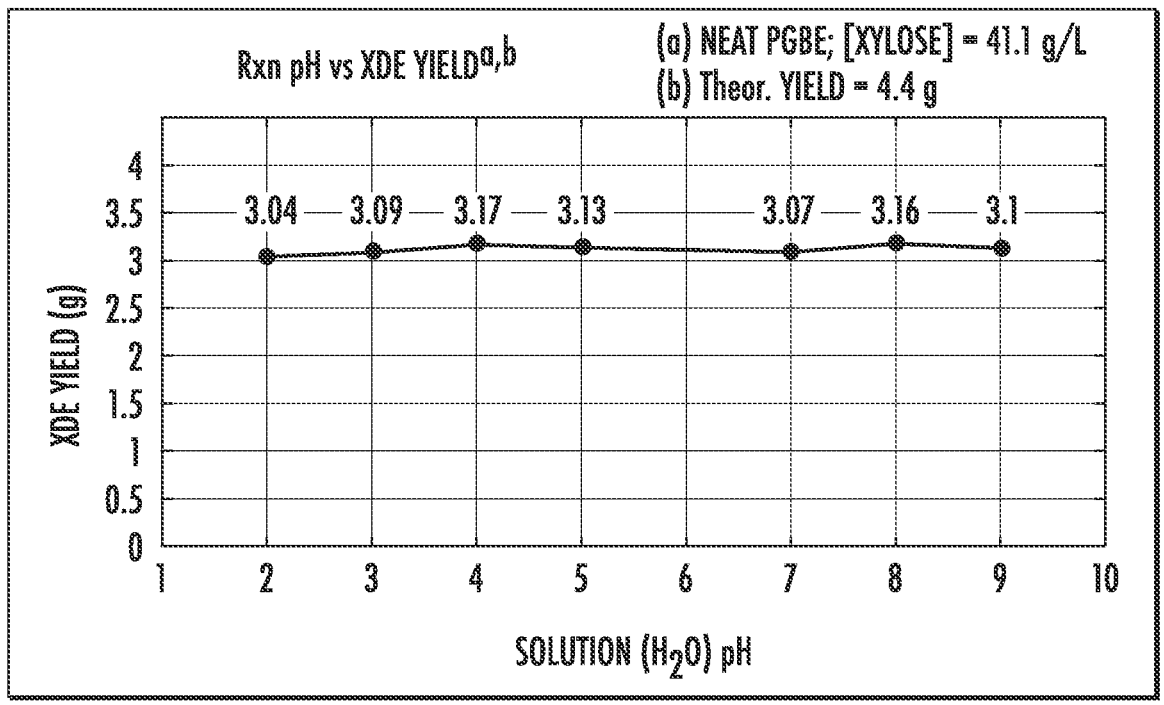
FIG. 6A is a graph showing XDE yield versus solution pH using neat PGBE.
Figure 6B:
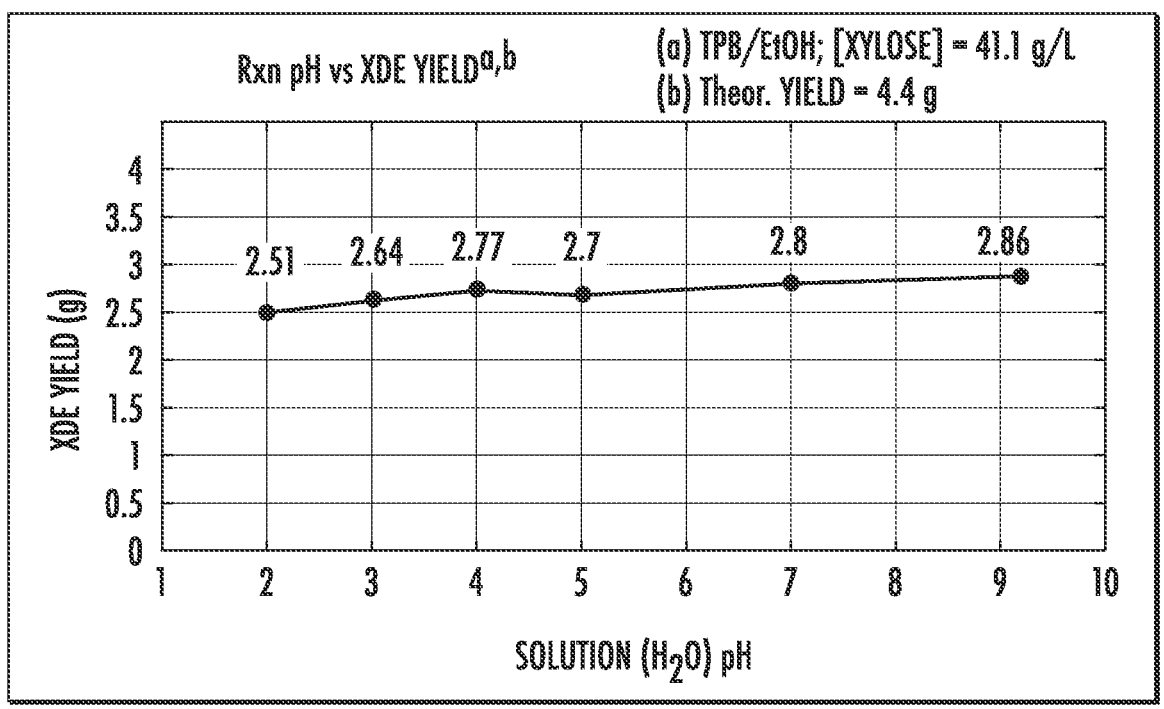
FIG. 6B is a graph showing XDE yield versus solution pH using TPB/10 mL EtOH.

It has also been found that the formation and isolation of XDE via filtration occurs at similar yields over a range of pH values for the starting xylose solution as shown in FIGS. 6A-6B.

Figure 7A:
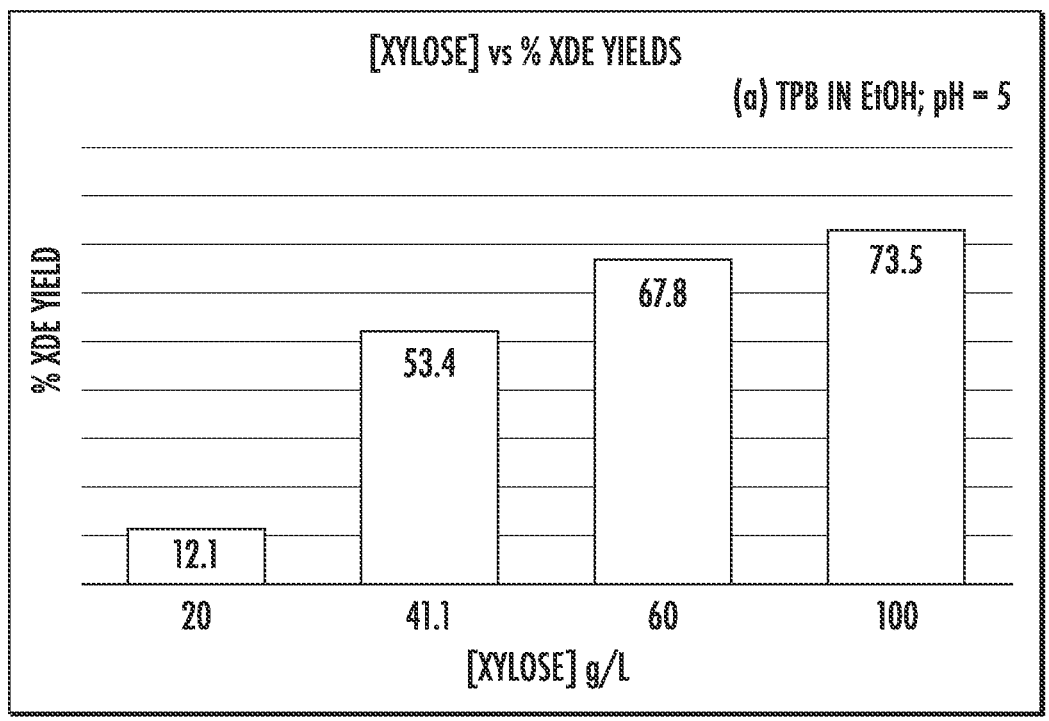
FIG. 7A is a graph showing XDE % yield versus xylose concentration at a pH=5 using TPB/EtOH.
Figure 7B:
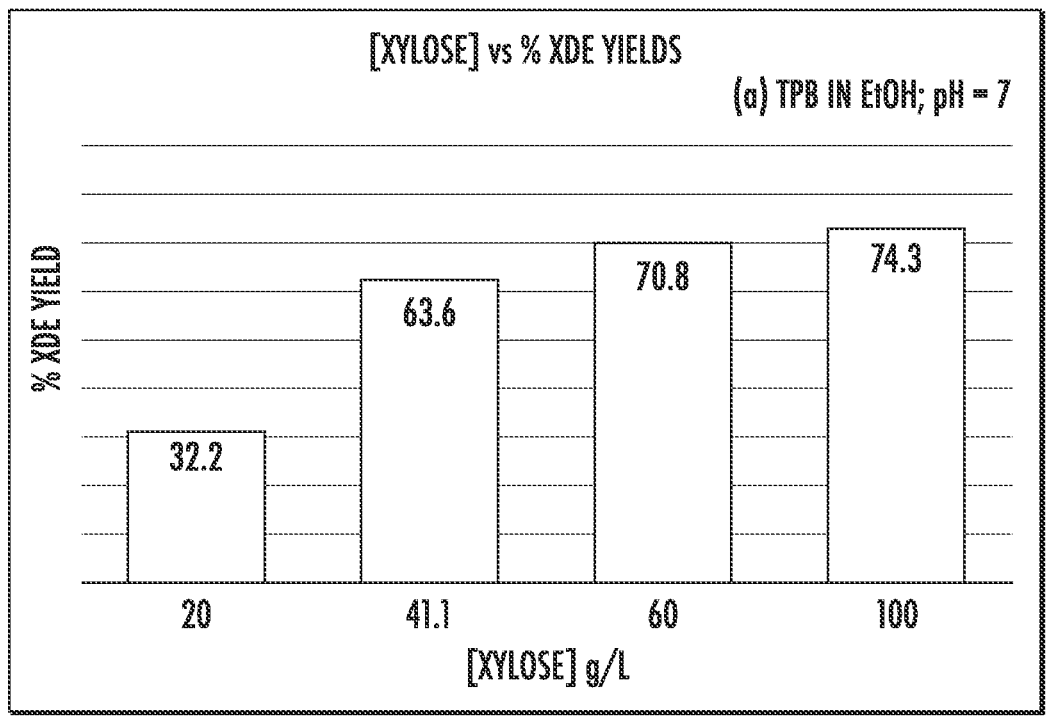
FIG. 7B is a graph showing XDE % yield versus xylose concentration at a pH=7 using TPB/EtOH.
Figure 7C:
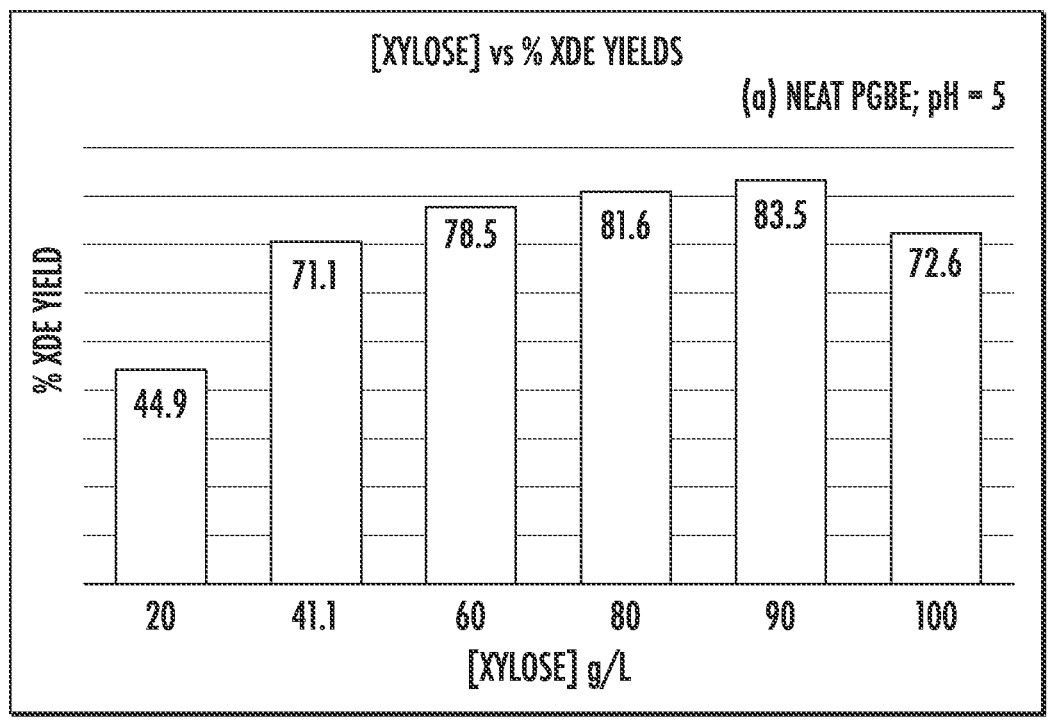
FIG. 7C is a graph showing XDE % yield vs xylose concentration at a pH=5 using neat PGBE.

Xylose Concentration: An increase in the concentration of xylose present in solution was also found to lead to an increase in the isolated yield of XDE via filtration as shown in FIGS. 7A-7C.

Example 3

Example 3 was carried out on the following aqueous samples: Sample 1. 25 Kg fermentation mixture; and Sample 2. 2 Kg sugar concentrate.

Sample 1

| sugar and carboxylate composition (g/L) | |
|---|---|
| Xylose | 41.1 |
| Arabinose | 2.7 |
| Xylitol | 2.2 |
| Lactate | 7.8 |
| Acetate | 7.2 |

Sample 2

| sugar and carboxylate composition (g/L) | |
|---|---|
| Disaccharide | 8.2 |
| Glucose | 364.8 |

Sample 2-continued

| sugar and carboxylate composition (g/L) | |
|---|---|
| Xylose | 166.7 |
| Galactose (P) | 4.0 |
| Arabinose (P) | n.a. |
| Fructose (P) | n.a. |
| Arabinose (H) | 7.5 |
| NaDL | 0.8 |
| Formic Acid | n.a. |
| Acetic Acid | 1.2 |

Sample 1 pH determination: pH=5.2 (same as shipped)

Sample 1 HPLC analysis:

HPLC Experimental Conditions

Column: Agilent Technologies HPX 87H 300×7.7 mm (Agilent Technologies, Santa Clara, California, United States of America)

Guard Column: PL HI-PLEX H GUARD Cartridges 5×3 MM

Mobile Phase: 0.005 M H2SO4 in water

Flow rate: 0.7 mL/min

Oven temperature: 60° C.

| Sample 1 composition (g/L) | |
|---|---|
| Xylose | 42.2 |
| Arabinose | 1.7 |
| Xylitol | see note below |
| Lactic Acid | 7.1 |
| Acetic Acid | 7.0 |

High xylose concentration in the fermentation mixture was confirmed (42.2 g/L). Unable to determine xylitol concentration due to overlap with arabinose.

For reaction purposes, overall polyol concentration relevant value needed. From supplier, [polyol]=46 g/L; from analysis, [polyol]=44.0 g/L. Based on acidic conditions used during HPLC analysis acetic acid and lactic acid concentrations were determined in lieu of acetate and lactate concentration Good agreement between acetic/lactic acid and acetate/lactate values.

Processes in accordance with the presently disclosed subject matter were applied on aliquots of the fermentation mixture (Sample 1) to isolate xylose in pure, crystalline form. Several ethanolic formulations of phenylboronic acid were prepared and tested to evaluate stoichiometry for precipitation of XDE (Step A, FIG. 1).

XDE Precipitation and Isolation from Sample 1

The pH of a clear, brown volume of Sample 1 was adjusted according to the table below. This was added to a clear, colorless solution of PBA dissolved in ethanol and a light colored solid precipitated from solution almost instantaneously. The light tan suspension was stirred for 2 hours. The precipitated solid was collected via filtration and dried in a 95° C. oven. The tan solid was suspended in EtOAc and any insolubles were removed by filtration. The solvent was removed under vacuum to yield an off-white solid that was characterized by $^1H$ NMR spectroscopy ($CDCl_3$).

| Entry | Fermentation Residue | | | | | XDE | | RHS[b] | |
|---|---|---|---|---|---|---|---|---|---|
| | Vol. (ml) | pH | Xyl[a] (g) | mmols polyol | mmols lactate | mmols PBA | Isolated (g) | Theory (g) | % Y | Xyl[c] (g) |
| 1 | 100 | 7.3 | 4.11 | 30.62 | 8.76 | 69.99 | 7.03 | 8.81 | 80 | 0.71 |
| 2 | 162 | 7.4 | 6.66 | 49.61 | 14.19 | 99.21 | 10.20 | 14.28 | 71 | 1.91 |
| 3 | 100 | 5.2 | 4.11 | 30.62 | 8.76 | 69.99 | 6.60 | 8.81 | 75 | 1.03 |
| 4 | 100 | 5.2 | 4.11 | 30.62 | 8.76 | 61.24 | 6.36 | 8.81 | 72 | 1.14 |

[a]Xyl = Xylose; [b]RHS = Residual Hydrolyzate Solution; [c]Xylose remaining in RHS as XDE.

Xylose Isolation from XDE (Step B, FIG. 1).

The boronic diester of xylose (XDE) was dissolved in the reaction solvent and 5 equivalents of propylene glycol (PG) were added to the solution. The solution was stirred overnight. A white solid was isolated and characterized by melting point analysis and $^1$H NMR spectroscopy (DMSO-$d_6$).

| Rxn Solvent | Temp | XDE amt/mmol | PG equiv./amt | Isolation Solvent | Theor Yield | Xylose amt/% yield | Yield |
|---|---|---|---|---|---|---|---|
| EtOAc | 25° C. | 7.03 g/21.84 | 5/8.3 g | EtOAc | 3.28 g | 2.64 | g/80% |
| EtOAc | 80° C. | 10.06 g/31.25 | 5/11.89 g | EtOAc | 4.69 g | 4.05 | g/86% |
| toluene | 25° C. | 75.92 g/235.8 | 5/90.1 g | EtOH | 35.40 g | 28.72 | g/81% |
| toluene | 25° C. | 9.52 g/29.60 | 5/11.27 g | Et$_2$O | 6.22 g | 5.19 | g/92% |

PBA Recovery
PBA Recovery from PG (Step C, FIG. 1).

For PBA (For FIG. 1, R can be —OH) recovery, 138.45 g PG (854.66 mmols) was stirred with acidic water (pH=2; HCl) overnight. A white solid was isolated via filtration. The solid was dried in a 65° C. oven. The melting point range of the white solid (84 g) was 209-215° C. The solid was analyzed by 1H NMR spectroscopy (DMSO-$d_6$) and it was determined the solid was composed of 47.5% PBA and 52.5% triphenylboroxine (TPB). The total number of mmols PBA present was 772.34 mmols (90% PBA recovery from PG).

PBA Recovery from RHS: Initial Results
Manipulations Performed on RHS Corresponding to Entries 3 and 4 in XDE Recovery Table.

The residual hydrolyzate solution (RHS) was acidified to a pH of 2 and the volume of the brown solution was reduced by roughly ¼ of the initial volume under vacuum. The solution was then allowed to stand overnight. A light-colored precipitate was observed and collected by filtration. The solid was dissolved in a mixture of EtOAc/EtOH and the volatiles removed under vacuum. The resulting residue was dissolved in CHCl3 and dried with MgSO4. After filtration and evaporation obtained an off-white solid which was characterized by melting point analysis and $_1$H NMR spectroscopy (CDCl$_3$).

Example 4

Abbreviations

PBA—Phenyl Boronic Acid
TPB—Triphenyl Boroxine
PG—Propylene Glycol
PGBE—propylene glycol boronic ester of PBA
XDE—xylose phenylboronic diester
ADE—arabinose phenylboronic diester The reaction schematic presented in FIG. 5 can be referred to in considering this Example.

Synthesis of PGBE

Triphenyl boroxine (TPB) (6.23 g, 20 mmol) and propylene glycol (PG) (4.78 g, 63 mmol) were added to a 100 mL round bottom flask and dissolved in EtOAc (30 mL) to produce a clear, golden solution. The solution was stirred at 25° C. overnight. After stirring overnight a small amount of brown insoluble residue was suspended in solution. The insolubles were removed by filtration. The solvent was removed under vacuum to yield a clear oil (10.79 g). Hexanes (40 mL) was added to the clear oil and a small amount of clear liquid would not dissolve in hexanes and settled to bottom of the RBF. Decanted hexanes for the denser insoluble oil. The solvent was removed under vacuum to yield a pale golden liquid. The liquid was characterized by $^1$H NMR (CDCl$_3$) and determined to be the corresponding PG boronate ester 4-methyl-2-phenyl-1,3,2-dioxaborolane (PGBE) (9.30 g, 96%).

XDE Formation
Boron Source: TPB
Triphenyl boroxine (TPB) (60.63 g, 194.50 mmol, ⅔ equiv/C5 sugar) was added to a 2 L round bottom flask and

| Entry | Solid Characterization/Composition | | | | | | PBA Recovery | |
|---|---|---|---|---|---|---|---|---|
| | Solid (g) | Mp (° C.) | mmols XDE[a] | mmols TPB | Mmols PBA | Combined[b] mmols PBA | Recovered[c] mmols PBA | % PBA[d] |
| #3 | 1.45 | 170-185 | 1.52 | 2.69 | 0.98 | 12.09 | 53.09 | 76 |
| #4 | 0.58 | — | 1.24 | 0.58 | 0 | 4.22 | 43.92 | 72 |

[a]ADE (arabinose boronic diester) was not observed in isolated solid; [b]Determined by $^1$H NMR spectroscopy where combined mmols PBA = (mmols XDE × 2) + (mmols TPB × 3) + mmols PBA; [c]Recovered mmols PBA = combined mmols PBA + (isolated mmols XDE × 2); [d]% PBA = recovered mmols PBA/initial mmols PBA used.

dissolved in 95% ethanol (178 mL) to produce a clear, colorless solution. Fermentation broth (1 L, 291.75 mmol C5 sugars, xylose (273.76 mmols) and arabinose (29.17 mmols)) was added to the TPB/EtOH solution with vigorous stirring at 25° C. The solution quickly became cloudy and light brown in appearance. After stirring for 1 h the solution was filled with a light tan precipitate. The light brown suspension was stirred for 4 h total. The solid was collected using a Buchner funnel, rinsed with a minimum amount of $H_2O$, and dried in a 110° C. oven overnight to afford a tan solid (57.65 g). The tan solid was suspended in EtOAc and insolubles were removed by filtration. The solvent was removed under vacuum to yield an off-white solid (54.29 g). The solid was characterized by $^1$H NMR ($CDCl_3$) and determined to be composed of >99% XDE (54.11 g) and ~0.3% TPB (0.17 g).

The residual fermentation broth (1.5 L) was allowed to slowly concentrate at atmospheric pressure over the course of several days until the volume had reached 0.2 L and the solution was filled with a light tan precipitate. The solid was collected using a Buchner funnel, rinsed with a minimum amount of $H_2O$, and dried in a 110° C. oven overnight to afford a tan solid. The tan solid was suspended in EtOAc and insolubles were removed by filtration. The solvent was removed under vacuum to yield an off-white solid (27.58 g). The solid was characterized by $^1$H NMR ($CDCl_3$) and determined to be composed of >99% XDE (27.4 g) and <1% TPB (0.18 g).

Boron Source: PGBE

The propylene glycol boronic ester of PBA (PGBE) (94.52 g, 583.49 mmol, 2 equiv/C5 sugar) was added to a 5 L round bottom flask. Fermentation broth (1 L, 291.75 mmol C5 sugars, xylose (273.76 mmols) and arabinose (29.17 mmols)) was added to the neat PGBE with vigorous stirring at 25° C. The solution quickly became cloudy and light brown in appearance. After stirring for 1 h the solution was filled with a light tan precipitate. The light brown suspension was stirred for 4 h total. The solid was collected using a Buchner funnel, rinsed with a minimum amount of $H_2O$, and dried in a 110° C. oven overnight to afford a tan solid (61.83 g). The tan solid was suspended in EtOAc and insolubles were removed by filtration. The solvent was removed under vacuum to yield an off-white solid (60.17 g). The solid was characterized by $^1$H NMR ($CDCl_3$) and determined to be composed of 100% XDE.

The residual fermentation broth (1.2 L) was allowed to slowly concentrate at atmospheric pressure over the course of several days until the volume had reached 0.2 L and the solution was filled with a light tan precipitate. The solid was collected using a Buchner funnel, rinsed with a minimum amount of $H_2O$, and dried in a 110° C. oven overnight to afford a tan solid (8.25 g). The tan solid was suspended in EtOAc and insolubles were removed by filtration. The solvent was removed under vacuum to yield an off-white solid (8.07 g). The solid was characterized by $^1$H NMR ($CDCl_3$) and determined to be composed of 100% XDE.

Boron Source: PGBE

The propylene glycol boronic ester of PBA (PGBE) (9.45 g, 58.35 mmol, 2 equiv/C5 sugar) was added to a 500 mL round bottom flask. Fermentation broth (0.1 L, 29.18 mmol C5 sugars, xylose (27.38 mmols) and arabinose (2.92 mmols)) was added to the neat PGBE with vigorous stirring at 25° C. The solution quickly became cloudy and light brown in appearance. After stirring for 1 h the solution was filled with a light tan precipitate. The light brown suspension was stirred for 4 h total. The solution volume was reduced by 0.6 L under vacuum at 55° C. The solid was collected using a Buchner funnel, rinsed with a minimum amount of $H_2O$, and dried in a 110° C. oven overnight to afford a tan solid (6.70 g). The tan solid was suspended in EtOAc and insolubles were removed by filtration. The solvent was removed under vacuum to yield an off-white solid (6.67 g). The solid was characterized by $^1$H NMR ($CDCl_3$) and determined to be composed of 100% XDE Boron Source: PGBE Salting Reagent: NaCl. Salting is an optional step that can be employed if desired to increase the yield of initially isolated XDE from the aqueous xylose solution by making the XDE even more insoluble in the hydrolyzate (e.g., fermentation broth). Thus, this optional step relates to process optimization, as might be desired. But, adding salt to a xylose solution does not precipitate xylose alone, as the boron reagent precipitates the xylose. The yield of XDE can also be increased by simply concentrating the reaction mixture after addition of the boron reagent and removing water.

The propylene glycol boronic ester of PBA (PGBE) (9.45 g, 58.35 mmol, 2 equiv/C5 sugar) was added to a 250 mL round bottom flask. NaCl (10 g, [NaCl]=100 g/L) was added to 0.1 L of fermentation broth (29.18 mmol C5 sugars, xylose (27.38 mmols) and arabinose (2.92 mmols)) and stirred until all the NaCl dissolved. This clear, dark brown solution was added to the neat PGBE with vigorous stirring at 25° C. The solution quickly became cloudy and light brown in appearance. After stirring for 1 h the solution was filled with a light tan precipitate. The light brown suspension was stirred for 4 h total. The solid was collected using a Buchner funnel, rinsed with a minimum amount of $H_2O$, and dried in a 110° C. oven overnight to afford a tan solid (7.34 g). The tan solid was suspended in EtOAc and insolubles were removed by filtration. The solvent was removed under vacuum to yield an off-white solid (7.23 g). The solid was characterized by $^1$H NMR ($CDCl_3$) and determined to be composed of 100% XDE.

Xylose Formation

To a stirred solution of XDE (12.5 g, 38.83 mmol) in EtOAc (125 mL) at 25° C. was added propylene glycol (PG) (14.88 g, 195.56 mmols). The clear solution was heated to 80° C. and stirred for 12 hours. Heating can increase the rate of the reaction to decrease time required but does not change the reaction course or products versus running the reaction at 25° C. After 12 h, the solution was filled with a white solid. The suspension was cooled to 25° C. and the solid was collected using a Buchner funnel, rinsed with a minimum amount of EtOAc, and dried in a 110° C. oven overnight to afford a white solid (5.18 g). The melting point range of the isolated solid was determined to be 148-151° C. The solid was characterized by $^1$H NMR (DMSO-$d_6$) and determined to be D-xylopyranose as a 99:1 mixture of α:β anomers.

The EtOAc filtrate was concentrated by rotary evaporation to obtain a biphasic liquid mixture comprising PG and the corresponding PG boronate ester 4-methyl-2-phenyl-1, 3,2-dioxaborolane (PGBE). When the mixture was allowed to stand the less dense, hydrophobic PGBE formed a clear, colorless liquid layer on top of the hydrophilic PG which was clear and yellow in appearance. The PG (9.0 g) and PGBE (11.56 g) were separated from each other. The PG was characterized by $^1$H NMR (DMSO-$d_6$) and determined to be composed of >98% PG, <1% xylose, and a trace of PGBE. The PGBE was characterized by $^1$H NMR ($CDCl_3$) and determined to be composed of >99% PGBE and <1 XDE.

Example 5

Fermentation Residue Characterization

An aqueous solution comprising a fermentation residue (FR) was characterized by HPLC and the high xylose concentration in the fermentation residue was confirmed (41.1 g/L). We were unable to determine the xylitol concentration due to overlap with xylose and arabinose (2.7 g/L). Based on acidic conditions used during HPLC analysis, acetic acid and lactic acid concentrations were determined in lieu of acetate and lactate concentrations. We found good agreement between acetic/lactic acid and acetate/lactate values. The research described below uses the fermentation residue with no further modification. We determined that under the reaction conditions used the acetic acid and lactic acid would not react with our phenyl boron reagent. We used 2 equivalents of phenyl boron reagent for each equivalent of xylose and arabinose present in the fermentation residue. Experiments were run and it was determined that the presence of a small amount of xylitol (2.2 g/L) does not affect the overall yield of xylose isolated. The reaction schematic presented in FIG. 5 can be referred to in considering this Example.

Process Step A

Production of the hydrophobic xylose furanose diester, $(PhB)_2(D-XylfH_{-4})$ (XDE), using the phenylboronic ester of propylene glycol (PGBE) (Step A, FIG. 5) involves the addition of the Fermentation Residue (FR) to two equivalents of PGBE (amount of PGBE based on xylose/arabinose concentrations) to form the xylose boronic diester (XDE). XDE cleanly precipitates from the mixture and is isolated by simple filtration in 77% yield. Although arabinose is present at low concentrations in the hydrolyzate (pH=5) only XDE precipitates and the arabinose boronic diester remains in solution allowing for our simple separation method. The xylose depleted Fermentation Residue (FR) contains arabinose, unrecovered xylose, unreacted phenyl boronic acid (PBA) and/or the corresponding boronic esters of each sugar. The reaction schematic presented in FIG. 3 can also be referred to in considering this step.

Several methods such as 1) the use of acids to decrease the pH of the Fermentation Residue (FR); and 2) the use of salt additives in order to decrease the solubility of XDE in the FR and increase the yield of isolated XDE were investigated. The use of various diols, triols, and polyols were also investigated in the formation of corresponding phenyl boronic esters. These new phenyl boronic esters were then explored as a replacement for PGBE in the formation of XDE from FR.

Process Step B

Trans-esterification using propylene glycol (PG) and xylose precipitation (Step B, FIG. 5) exploits an observation that formation of a thermodynamically more stable boronic ester can drive the cleavage of boronic esters of six- and even certain five-membered ring 1,2-diols, such as are present in XDE. The isolated xylose boronic diester (XDE) isolated in Step A is dissolved in ethyl acetate (5 mL ethyl acetate dissolves 1 gram of XDE at 25° C.) and any ethyl acetate insoluble material is filtered away from the clear, yellow XDE solution. Five equivalents of propylene glycol (PG) were reacted with the ethyl acetate solution of XDE at 80° C. In this reaction, xylose precipitates as D-xylopyranose and the ethyl acetate solution contains the corresponding phenylboronic ester of propylene glycol (PGBE) along with unreacted propylene glycol (PG). After the xylose is separated away from the ethyl acetate solution of PGBE/PG by filtration, the crystalline xylose (82-85%) is allowed to dry. The reaction schematic presented in FIG. 4 can also be referred to in considering this step.

Regarding the ethyl acetate solution that contains PGBE/PG, the ethyl acetate was separated from PGBE/PG using vacuum distillation (96% recovery). The propylene glycol boronic ester (PGBE) is nonpolar and does not mix with the unreacted propylene glycol (PG), which is polar, and a biphasic mixture was observed after removal of the ethyl acetate. PGBE has a higher density than PG. The two immiscible liquids can be separated from each other and PGBE can be recovered (90%) and used again in Step A for the production of XDE from a new batch of Fermentation Residue (FR). Recovered propylene glycol does contain dissolved xylose and can be used for the conversion of XDE to xylose.

The use of other solvents, such as acetone and isopropyl acetate, in the conversion of XDE to xylose was also investigated, as was the use of diols, triols, and polyols other than PG in the conversion of XDE to xylose.

$^1$H NMR spectral characterization of the precipitated xylose indicated a high level of purity (>99%, ca. 98:2 mixture of α:β anomers): no contamination from other sugars or organic byproducts from the Fermentation Residue (FR) was noted. As mentioned above, the unreacted PG was recovered and used again as it readily separates from the non-polar, denser PGBE after removal of solvent from the filtrate.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Reichvilser, M. M., et al., Boronic acid mono- and diesters of the aldopentoses. Carbohydrate Research, 2010, 345 (4), p 498-502.
2. Roy, C. D., et al., A comparative study of the relative stability of representative chiral and achiral boronic esters employing transesterification. Monatshefte Fur Chemie, 2007, 138(9), p 879-887.
3. Roy, C. D., et al., Stability of boronic esters—Structural effects on the relative rates of transesterification of 2-(phenyl)-1,3,2-dioxaborolane. Journal of Organometallic Chemistry, 2007, 692(4), p 784-790.
4. Washburn, R. M., et al., Benzeneboronic Anhydride. Organic Synthesis, 1959, 39(3), p 3-6.
5. Kaupp, G., et al., Waste-free and facile solid-state protection of diamines, anthranilic acid, diols, and polyols with phenylboronic acid. Chemistry-a European Journal, 2003, 9(17), p 4156-4160.
6. Sun, J. et al., A Method for the Deprotection of Alkylpinacolyl Boronate Esters. Journal of Organic Chemistry, 2011, 76(9), p 3571-3575.
7. U.S. patent application Ser. No. 15/093,005.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A process for isolating xylose from an aqueous solution, the process comprising:
   providing an aqueous solution comprising the xylose;
   combining a boron compound with the aqueous solution to form a boron derivative of the xylose, wherein the combining of the boron compound with the aqueous solution is performed at a pH of about 2.0 to below 4.8;
   isolating the boron derivative of the xylose from the aqueous solution as a precipitate;
   dissolving the boron derivative of the xylose in a solvent; and
   isolating the xylose from the solvent as a precipitate using a boron capture agent.

2. The process of claim 1, wherein the aqueous solution is provided by a hydrolysis process.

3. The process of claim 2, wherein the hydrolysis process comprises subjecting a biomass to dilute acid hydrolysis to form a biomass hydrolyzate; subjecting a biomass to enzymatic hydrolysis and/or to digestion to form the biomass hydrolyzate; or a combination thereof.

4. The process of claim 3, wherein the biomass is a hemi-cellulose rich agricultural biomass.

5. The process of claim 4, wherein the hemi-cellulose rich agricultural biomass comprises a material selected from the group consisting of soy hulls from soybean processing, rice hulls obtained from rice milling, corn fiber obtained from wet milling or from dry milling, bagasse from sugarcane processing, pulp from sugar beet processing, distillers grains, switch grass, straw, hard woods, and combinations thereof.

6. The process of claim 2, wherein the aqueous solution remaining after isolating the xylose is recycled into a further hydrolysis process step.

7. The process of claim 1, wherein the boron compound is selected from the group consisting of a boroxine, a glycol boronic ester, a 1,2-diol boronic ester, a 1,3-diol boronic ester, a polyol boronic ester of an alkyl or aryl boronic acid, and any combination thereof.

8. The process of claim 7, wherein the glycol boronic ester or the 1,2-diol boronic ester, or the 1,3-diol boronic ester, or the polyol boronic ester of an alkyl or aryl boronic acid is an ethylene glycol boronic ester, a propylene glycol boronic ester, a butylene glycol boronic ester, or a propanetriol boronic ester of phenyl boronic acid.

9. The process of claim 7, further comprising the step of recovering an amount of the boroxine, or the glycol boronic ester, or the 1,2-diol boronic ester, or the 1,3-diol boronic ester, or the polyol boronic ester of an alkyl or aryl boronic acid after isolating the xylose from the solvent as a precipitate.

10. The process of claim 1, wherein the boron compound can comprise a liquid boron compound or a solid boron compound, wherein when the boron compound is a solid boron compound, the method comprises adding an amount of a water-soluble alcohol to the solid boron compound to dissolve the solid boron compound.

11. The process of claim 1, wherein the solvent used in dissolving the boron derivative of the xylose is selected from the group consisting of an aromatic solvent, a ketone solvent, an ester solvent, and combinations thereof.

12. The process of claim 11, wherein the ester solvent is ethyl acetate.

13. The process of claim 1, wherein the boron capture agent is 1,2 propane diol.

14. The process of claim 1, further comprising the step of recovering an amount of the boron compound after isolating the xylose from the solvent as a precipitate.

15. The process of claim 1, wherein a boron compound: xylose molar ratio is 2.

* * * * *